United States Patent
Kobayashi et al.

(10) Patent No.: US 7,408,059 B2
(45) Date of Patent: Aug. 5, 2008

(54) METHOD FOR PRODUCING 3,4-DIHYDRO-1,2,3-OXATHIAZIN-4-ONE-2,2-DIOXIDE COMPOUND OR SALT THEREOF

(75) Inventors: Kenji Kobayashi, Arai (JP); Hitoshi Watanabe, Himeji (JP); Noboru Kamei, Arai (JP); Yasushi Yamamoto, Joetsu (JP)

(73) Assignee: Daicel Chemical industries, Ltd., Osaka (JP)

( * ) Notice: Subject to any disclaimer, the term of this patent is extended or adjusted under 35 U.S.C. 154(b) by 373 days.

(21) Appl. No.: 11/058,179

(22) Filed: Feb. 16, 2005

(65) Prior Publication Data

US 2005/0182255 A1 Aug. 18, 2005

(30) Foreign Application Priority Data

| Feb. 17, 2004 | (JP) | ............................ 2004-040553 |
| Nov. 24, 2004 | (JP) | ............................ 2004-339556 |

(51) Int. Cl.
*C07D 291/06* (2006.01)

(52) U.S. Cl. .......................................... 544/2; 562/40
(58) Field of Classification Search ................ 544/2
See application file for complete search history.

(56) References Cited

U.S. PATENT DOCUMENTS

| 4,607,100 | A |   | 8/1986  | Clauss et al. |
| 4,695,629 | A |   | 9/1987  | Clauss et al. |
| 4,804,755 | A |   | 2/1989  | Reuschling et al. |
| 4,806,639 | A |   | 2/1989  | Reuschling et al. |
| 4,876,341 | A | * | 10/1989 | Schutz et al. .................. 544/2 |
| 5,011,982 | A |   | 4/1991  | Clauss et al. |
| 5,103,046 | A |   | 4/1992  | Clauss et al. |

FOREIGN PATENT DOCUMENTS

| JP | 3-54940    | B2 | * | 8/1991  |
| JP | 3-184948   | A  |   | 8/1991  |
| JP | 5-70627    | B2 |   | 10/1993 |
| JP | 6-25189    | B2 |   | 4/1994  |
| JP | 2002220381 | A2 | * | 8/2002  |

* cited by examiner

*Primary Examiner*—Kahsay T Habte
(74) *Attorney, Agent, or Firm*—Birch, Stewart, Kolasch & Birch, LLP

(57) ABSTRACT

A method produces a 3,4-dihydro-1,2,3-oxathiazin-4-one-2,2-dioxide compound of following formula (2):

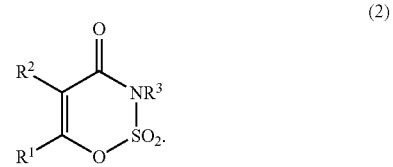

(2)

wherein $R^1$ and $R^2$ are the same as or different from each other and are each hydrogen atom or an organic group inert to the reaction; and $R^3$ is hydrogen atom or an organic group inert to the reaction, or a salt thereof, by subjecting a beta-ketoamide-N-sulfonic acid of following Formula (1):

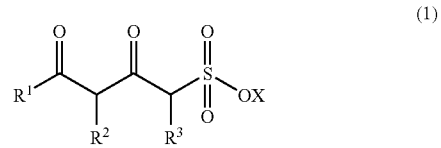

(1)

wherein $R^1$, $R^2$ and $R^3$ are as defined above; and X is hydrogen atom, or a salt thereof, to cyclization in the presence of an acid anhydride with or without further subjecting the cyclized product to hydrolysis, in which the cyclization is continuously carried out using a continuous flow reactor.

4 Claims, 1 Drawing Sheet

METHOD FOR PRODUCING 3, 4-DIHYDRO-1,2,3-OXATHIAZIN-4-ONE-2,2-DIOXIDE COMPOUND OR SALT THEREOF

BACKGROUND OF THE INVENTION

1. Field of the Invention

The present invention relates to a method for producing 3,4-dihydro-1,2,3-oxathiazin-4-one-2,2-dioxide compounds or salts thereof which are useful typically as sweeteners or raw materials therefor in food industry or intermediate materials for fine chemicals.

2. Description of the Related Art

A method for producing a 3,4-dihydro-1,2,3-oxathiazin-4-one-2,2-dioxide compound or a salt thereof is disclosed, for example, in Angewandte Chemie International Edition, 12, 10 (1973), 869-876 (or German Unexamined Patent Application Publication No. 2453063). In this method, an acetoacetamide-N-sulfonyl halide (fluoride or chloride) is cyclized by the action of a base such as methanolic KOH to thereby yield a 3,4-dihydro-1,2,3-oxathiazine, such as 6-methyl-3,4-dihydro-1,2,3-oxathiazin-4-one-2,2-dioxide or a salt thereof. The acetoacetamide-N-sulfonyl halide is prepared by allowing a halosulfonyl isocyanate to react with a suitable acetoacetylating agent. Such a method, however, is not suitable as an industrial method, since the halosulfonyl isocyanate and amidosulfonyl halide used as starting materials are special compounds and are difficult to handle.

Separately, Japanese Unexamined Patent Application Publication No. 03-184948, Japanese Examined Patent Application Publications No. 03-54940, No. 05-70627 and No. 06-25189 each disclose a method for producing 6-methyl-3,4-dihydro-1,2,3-oxathiazin-4-one-2,2-dioxide or a salt thereof by allowing acetoacetamide-N-sulfonic acid or a salt thereof to react with $SO_3$ in an inert organic solvent, subjecting the product to cyclization and then to ring-closing. Among them, Japanese Examined Patent Application Publication No. 03-54940 discloses a spray tower reactor and a thin-film reactor equipped with a mechanical stirrer as an apparatus for carrying out the cyclization at low temperatures within a short time and for achieving a high yield. These apparatuses employ not only external cooling but also heat removal by the action of latent heat of vaporization of a solvent, in order to remove a large quantity of heat generated in the cyclization and dehydration. When a spray tower or a thin-film evaporator equipped with a mechanical stirrer, such as a wiped film evaporator (WFE), is used as the reactor in the production of a 3,4-dihydro-1,2,3-oxathiazin-4-one-2,2-dioxide compound or a salt thereof, the apparatus (reactor) is expensive and exhibits insufficient stability in production. This is because the residence time and reaction control in the reactor significantly affects the reaction result but the apparatus is hard to control these parameters with respect to various possible variations in industrial production. In this connection, above-mentioned Japanese Examined Patent Application Publication No. 03-54940 describes a tubular reactor as an example of reactors to be used but fails to teach a concrete example and concrete advantages of the tubular reactor.

SUMMARY OF THE INVENTION

Accordingly, an object of the present invention is to provide a method for industrially efficiently producing a 3,4-dihydro-1,2,3-oxathiazin-4-one-2,2-dioxide compound or a salt thereof with good operational stability without the use of an expensive apparatus.

After intensive investigations to achieve the above object, the present inventors have found that a 3,4-dihydro-1,2,3-oxathiazin-4-one-2,2-dioxide compound or a salt thereof can be produced in a high yield with good operational stability by continuously carrying out the reaction with the use of a continuous flow reactor. The present invention has been accomplished based on these findings.

Specifically, the present invention provides a method for producing a 3,4-dihydro-1,2,3-oxathiazin-4-one-2,2-dioxide compound represented by following formula (2):

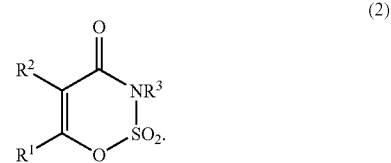

(2)

wherein $R^1$ and $R^2$ are the same as or different from each other and are each hydrogen atom or an organic group inert to the reaction; and $R^3$ is hydrogen atom or an organic group inert to the reaction, or a salt thereof, the method including the step of subjecting a beta-ketoamide-N-sulfonic acid represented by following Formula (1):

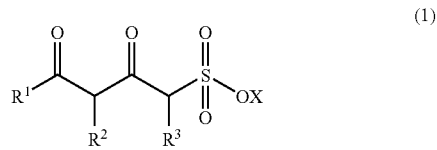

(1)

wherein $R^1$, $R^2$ and $R^3$ are as defined above; and X is hydrogen atom, or a salt thereof, to cyclization in the presence of an acid anhydride with or without further subjecting a cyclized product to hydrolysis, wherein the cyclization is continuously carried out using a continuous flow reactor.

A tubular reactor or a motionless mixer, for example, is used as the continuous flow reactor. The continuous flow reactor may have at least one of a stirred mixer, an ultrasonic mixer and a motionless mixer in an inlet part thereof.

The substituents $R^1$ and $R^2$ can each be, for example, hydrogen atom, an alkyl group, an alkenyl group, an alkynyl group, a cycloalkyl group, an acyl group, an aralkyl group or an aryl group, and $R^3$ can be, for example, hydrogen atom, an alkyl group, an alkenyl group, an alkynyl group, a cycloalkyl group, an acyl group, an aralkyl group or an aryl group.

The acid anhydride can be, for example, an acid anhydride derived from at least one acid selected from the group consisting of sulfuric acid, sulfonic acids, halogenated sulfuric acids, pyrophosphoric acid, nitric acid and boric acids.

The 3,4-dihydro-1,2,3-oxathiazin-4-one-2,2-dioxide compound can be typified by 6-methyl-3,4-dihydro-1,2,3-oxathiazin-4-one-2,2-dioxide.

The method of the present invention continuously carries out the cyclization in a continuous flow reactor, can reduce cost of equipment and industrially efficiently produce a 3,4-dihydro-1,2,3-oxathiazin-4-one-2,2-dioxide compound or a salt thereof with good operational stability.

Further objects, features and advantages of the present invention will become apparent from the following description of the preferred embodiments with reference to the attached drawings.

DESCRIPTION OF THE PREFERRED EMBODIMENTS

Figure 1:
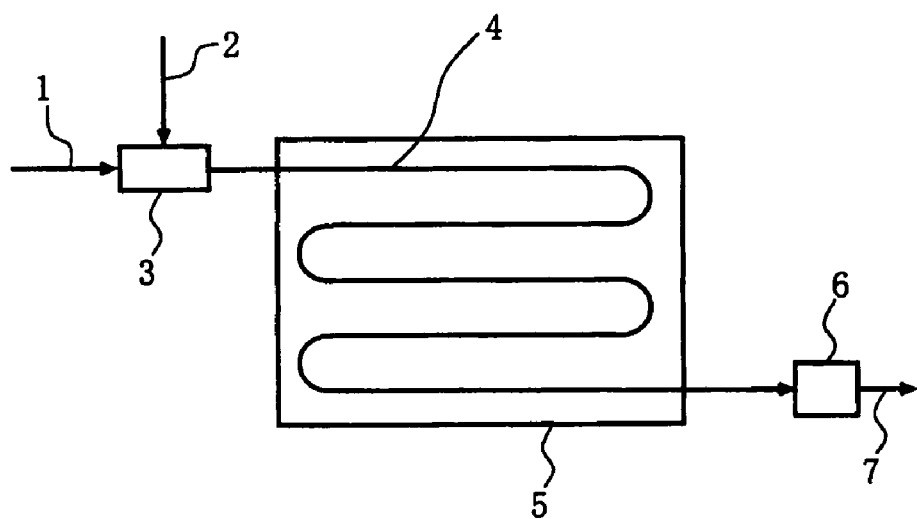
FIG. 1 is a schematic diagram of an example of production equipment for use in the production method according to the present invention.

According to the present invention, the 3,4-dihydro-1,2,3-oxathiazin-4-one-2,2-dioxide compound represented by Formula (2) or a salt thereof is produced by subjecting the beta-ketoamide-N-sulfonic acid represented by Formula (1) or a salt thereof to cyclization in the presence of an acid anhydride with or without further subjecting a cyclized product to hydrolysis.

In Formula (1), the organic groups inert to the reaction in $R^1$, $R^2$ and $R^3$ can be any organic groups inert to the reaction and include, for example, alkyl groups, alkenyl groups, alkynyl groups, cycloalkyl groups, acyl groups, aralkyl groups and aryl groups. Examples of the alkyl groups are linear or branched-chain alkyl groups each having one to ten carbon atoms, including alkyl groups each having one to six carbon atoms such as methyl group, ethyl group, propyl group, butyl group, isobutyl group and tert-butyl group. The alkenyl groups include linear or branched-chain alkenyl groups each having two to ten carbon atoms, including alkenyl groups each having two to five carbon atoms, such as vinyl group, allyl group, isopropenyl group, 1-butenyl group and 2-butenyl group. The alkynyl groups include linear or branched-chain alkynyl groups each having two to ten carbon atoms, including alkynyl groups each having two to five carbon atoms, such as ethynyl group, propynyl group, 1-butynyl group and 2-butynyl group. Examples of the cycloalkyl groups are cycloalkyl groups each having three to ten carbon atoms, such as cyclopropyl group, cyclobutyl group, cyclopentyl group and cyclohexyl group, of which cycloalkyl groups each having four to eight carbon atoms are preferred. Examples of the acyl groups are linear or branched-chain aliphatic acyl groups each having two to ten carbon atoms, such as acetyl group, propionyl group, butyryl group, isobutyryl group and valeryl group; and aromatic acyl groups each having seven to eleven carbon atoms, such as benzoyl group, toluyl group and naphthoyl group. Examples of the aralkyl groups are $C_6$-$C_{10}$ aryl-$C_1$-$C_4$ alkyl groups such as benzyl group. Examples of the aryl group are aryl groups each having six to ten carbon atoms, such as phenyl group.

The salt of the beta-ketoamide-N-sulfonic acid represented by Formula (1) includes salts (sulfonates) in which the sulfonic group is neutralized with a base, and salts in which $R^3$ is hydrogen atom, and the —NH— group in the formula is neutralized with a base. These salts (the salts of sulfonic acid, and salts of —NH—) typically include metal salts, ammonium salts and salts of organic bases. Examples of the metal salts are salts of alkali metals (Group 1A metals of the Periodic Table of Elements) such as Li, Na and K; salts of alkaline earth metals (Group 2A metals of the Periodic Table of Elements) such as Mg, Ca, Sr and Ba; salts of metals of Group 3B of the Periodic Table of Elements such as Al and Ga; and salts of transition metals. Examples of the transition metals are, of the Periodic Table of Elements, Group 3A metals, Group 4A metals, Group 5A metals, Group 6A metals, Group 7A metals such as Mn, Group 8 metals such as Fe, Group 1B metals such as Cu, Ag and Au, Group 2B metals such as Zn, Group 4B metals, and Group 5B metals. Preferred metal salts are salts of mono-, di- or tri-valent metals, including salts of alkali metals such as Na and K; salts of alkaline earth metals such as Mg and Ca; Al salts; and salts of transition metals such as Mn and Fe. Among them, salts of alkali metals such as Na and K are typically preferred from the viewpoints of economical efficiency and safety.

Examples of the organic bases are aliphatic amines, alicyclic amines, aromatic amines, cyclic amines and nitrogen-containing aromatic heterocyclic compounds. The aliphatic amines include, for example, primary amines including mono-$C_1$-$C_{10}$ alkyl-amines such as methylamine and ethylamine; secondary amines including di-$C_1$-$C_{10}$ alkyl-amines such as dimethylamine and ethylmethylamine; and tertiary amines including tri-$C_1$-$C_{10}$ alkyl-amines such as trimethylamine and triethylamine. Examples of the alicyclic amines are mono- di- or tri-$C_3$-$C_{12}$ cycloalkyl-amines such as cyclohexylamine. Examples of the aromatic amines are mono-$C_6$-10 aryl-amines such as aniline and dimethylaniline; di-$C_6$-10 aryl-amines such as diphenylamine; tri-$C_6$-10 aryl-amines such as triphenylamine; and aralkylamines such as benzylamine. Examples of the cyclic amines are piperidine, N-methylpiperidine and morpholine. Examples of the nitrogen-containing aromatic heterocyclic compounds are pyridine, quinoline, and derivatives thereof. Preferred organic bases are aliphatic amines and any tertiary amines.

The substituents $R^1$, $R^2$ and $R^3$ in Formula (1) can be used in any suitable combination but it is preferred that $R^1$ and $R^2$ are each hydrogen atom or an alkyl group having one to four carbon atoms, and $R^3$ is hydrogen atom or an alkyl group having one to four carbon atoms. The compound of Formula (1) is typically preferably an acylacetamide-N-sulfonic acid wherein $R^1$ is an alkyl group having one to four carbon atoms, and $R^2$ and $R^3$ are hydrogen atoms, of which acetoacetamide-N-sulfonic acid wherein $R^1$ is methyl group is specifically preferred. The salt (sulfonate) of the compound of Formula (1) is preferably a salt with a tertiary amine.

The acid anhydride herein serves as a cyclizing agent, such as a cyclization-dehydration agent, for the beta-ketoamide-N-sulfonic acid represented by Formula (1) or a salt thereof (hereinafter briefly referred to as "substrate"). Examples of the acid anhydride are acid anhydrides derived from inorganic acids or organic acids. The inorganic acids include, for example, sulfuric acid; halogenated sulfuric acids such as fluorosulfuric acid and chlorosulfuric acid; pyrophosphoric acids including pyrophosphoric acid and halogenated pyrophosphoric acids such as fluoropyrophosphoric acid; nitric acid; and boric acids such as orthoboric acid and metaboric acid. The organic acids include, for example, sulfonic acids; organic phosphoric acids including $C_1$-$C_4$ alkyl-phosphoric acids such as methylphosphoric acid, and mono-$C_1$-$C_4$ alkyl esters of phosphoric acid, such as monomethyl phosphate and monoethyl phosphate. The acid anhydride can be any of an acid anhydride derived from one molecule of an acid as a result of dehydration, an acid anhydride derived from two or more molecules of an acid as a result of dehydration; and an acid anhydride derived from two or more molecules of different acids as a result of dehydration (composite acid anhydride). Each of these acid anhydrides can be used alone or in combination. The acid anhydride is preferably an acid anhydride derived from an acid containing sulfuric acid, of which sulfuric anhydride ($SO_3$) is typically preferred.

The amount of the acid anhydride is 1 mole or more (e.g., about 1 to about 20 moles), preferably about 1 to about 10 moles, and typically preferably about 4 to about 6 moles per 1 mole of the substrate.

The cyclization, such as cyclization-dehydration, of the beta-ketoamide-N-sulfonic acid of Formula (1) or a salt thereof can be carried out in the absence of a solvent or is preferably carried out in the presence of a solvent. Any inorganic or organic solvent that is inert to the reaction, typically inert to the acid anhydride, can be used as the reaction solvent, but an organic solvent inert to the reaction is generally used. The solvent is generally a substantially anhydrous solvent.

Examples of the organic solvent are aliphatic hydrocarbons such as pentane, hexane and octane; alicyclic hydrocarbons such as cyclohexane; aromatic hydrocarbons such as benzene, toluene, xylenes and ethylbenzene; halogenated hydrocarbons including haloalkanes such as dichloromethane, dichloroethane, chloroform, trichloroethylene, tetrachloroethylene and trichlorofluoroethylene; esters including carboxylic acid esters such as methyl acetate, ethyl acetate, butyl acetate and methyl propionate; ketones including aliphatic ketones such as acetone, methyl ethyl ketone and methyl isobutyl ketone, and cyclic ketones such as cyclohexanone; ethers including open-chain ethers such as diethyl ether, diisopropyl ether, 1,2-dimethoxyethane, Cellosolves (ethylene glycol monoethyl ether and derivatives thereof), Carbitols (diethylene glycol ethyl ether and derivatives thereof), and Diglyme (diethylene glycol dimethyl ether and derivatives thereof), aromatic ethers such as anisole, 1,2-dimethoxybenzene and diphenyl ether, and cyclic ethers such as tetrahydrofuran, dioxolane and dioxane; sulfoxides such a dimethyl sulfoxide, sulfolane, 2-methylsulfolane and 3-methylsulfolane. Each of these solvents can be used alone or in combination. Preferred solvents are halogenated hydrocarbons, of which dichloromethane is typically preferred.

A key feature of the present invention is that the cyclization is continuously carried out using a continuous flow reactor. The continuous flow reactor is preferably a tubular reactor or a motionless mixer. In the method of the present invention using a tubular reactor or a motionless mixer as the reactor, it is preferred for a higher result of the cyclization that the substrate and acid anhydride for use in the reaction are separately dissolved or dispersed in the solvent and are cooled to, for example, 10° C. or below (about −100° C. to about 10° C.), preferably −80° C. to 10° C., and more preferably −30° C. to 10° C. before the reaction. The concentration of the substrate in a mixture containing the substrate to be fed to the reactor can be appropriately set within ranges not deteriorating, for example, operability and is generally from about 0.1 to about 50 percent by weight, preferably from 0.5 to 30 percent by weight, and more preferably from about 1 to about 15 percent by weight. Likewise, the concentration of the acid anhydride in a mixture containing the acid anhydride to be fed to the reactor can be appropriately set within ranges not deteriorating, for example, operability and is generally from about 0.1 to about 50 percent by weight, preferably from 0.5 to 30 percent by weight, and more preferably from about 1 to about 15 percent by weight.

The total amount of the reaction solvent can be appropriately set under consideration of reactivity and operability and is generally set within a wide range from about 1 to about 1000 parts by weight, preferably from about 5 to about 500 parts by weight, more preferably from about 5 to about 50 parts by weight, and specifically preferably from about 10 to about 20 parts by weight, per 1 part by weight of the substrate.

The cyclization is carried out by continuously feeding the beta-ketoamide-N-sulfonic acid represented by Formula (1) or a salt thereof and the acid anhydride to a tubular flow reactor or a motionless mixer equipped with a cooler for cooling from the outside, such as a cooling jacket or a cooling tank (refrigerant tank). The reaction temperature of the cyclization is generally from about −100° C. to about 0° C., preferably from about −80° C. to about −5° C., and more preferably from about −50° C. to about −15° C.

The material for the tubular reactor can be, but is not limited to, a stainless steel tube or a lined tube lined typically with glass or Teflon (registered trademark). The inner diameter of the tube to be used is not specifically limited but is preferably several ten millimeters or less (e.g., about 0.2 to about 30 millimeters), and more preferably about 10 millimeters or less (e.g., about 0.2 to about 10 millimeters) for satisfactory removal of the heat generated during cyclization. The length of the tube is set so as to satisfy the residence time required for the reaction. The residence time is generally from about 0.001 to about 60 seconds, preferably from about 0.01 to about 40 seconds, more preferably from about 0.1 to about 10 seconds, and specifically preferably from about 1 to about 10 seconds. The residence time is determined by calculation according to the following equation:

Residence time (sec)=[Capacity of the reactor (ml)]/ [Total amount of fed mixtures of raw materials (ml/sec)]

The tubular reactor may have an apparatus for accelerating the mixing of the beta-ketoamide-N-sulfonic acid of Formula (1) or a salt thereof with the acid anhydride (hereinafter referred to as "premixer") in an inlet part of the tubular reactor. Examples of the premixer are stirred mixers, ultrasonic mixers, motionless mixers such as a static mixer, and piping joints. The residence time in the premixer, if used, is for example from about 0.0005 to about 30 seconds, preferably from about 0.01 to about 20 seconds, more preferably from about 0.1 to about 10 seconds, and specifically preferably from about 1 to about 10 seconds. The residence time in the subsequent tubular reactor is, for example, from about 0.001 to about 60 seconds, preferably from about 0.01 to about 40 seconds, more preferably from about 0.1 to about 30 seconds, and specifically preferably from about 1 to about 30 seconds.

A motionless mixer such as a static mixer can also be used as the reactor. Such a motionless mixer has a higher capability of removing heat and can have a larger inner diameter than the tubular reactor, if used as the reactor. The inner diameter of the motionless mixer is, for example, from about 0.2 to about 30 mm, and preferably from about 0.5 to about 20 mm. The motionless mixer includes, but is not specifically limited to, a Sulzer static mixer and a Kenics static mixer. The residence time in the motionless mixer as the reactor is, for example, from about 0.001 to about 60 seconds, preferably from about 0.01 to about 40 seconds, more preferably from about 0.1 to about 10 seconds, and specifically preferably from about 1 to about 10 seconds. The motionless mixer, if used as the reactor, may also have a premixer in an inlet part thereof. In this case, the residence time in the premixer is, for example, from about 0.0005 to about 30 seconds, preferably from about 0.01 to about 20 seconds, more preferably from about 0.1 to about 10 seconds, and specifically preferably from about 1 to about 10 seconds, and the residence time in the subsequent motionless mixer is, for example, from about 0.001 to about 60 seconds, preferably from about 0.01 to about 40 seconds, more preferably from about 0.1 to about 10 seconds, and specifically preferably from about 1 to about 10 seconds.

The number of elements in the static mixer is not specifically limited but is preferably 10 or more, and more preferably 17 or more.

The cyclization allows water or a base (in the case, for example, where a salt of the compound of Formula (1) is used) to leave to thereby yield the 3,4-dihydro-1,2,3-oxathiazin-4-one-2,2-dioxide compound represented by Formula (2). Under some conditions of the type and/or amount of the acid anhydride, an adduct of the 3,4-dihydro-1,2,3-oxathiazin-4-one-2,2-dioxide compound represented by Formula (2) and the acid anhydride may be formed. In this case, the 3,4-dihydro-1,2,3-oxathiazin-4-one-2,2-dioxide compound can be obtained by subjecting the cyclized product further to hydrolysis.

The hydrolysis is carried out, for example, by subjecting the reaction mixture after the cyclization to an appropriate treatment according to necessity and mixing the mixture with water. The hydrolysis can be carried out by any system such as continuous system, batch system or semi-batch system. In the continuous hydrolysis, a stirring tank or a continuous reactor to be used in the cyclization can be used. The temperature of water and the reaction temperature are each, for example, from about 0° C. to about 50° C., and preferably from about 0° C. to about 10° C. The amount of water is, for example, from about 1 to about 100 moles, preferably from about 1 to about 50 moles, and more preferably from about 2 to about 20 moles per 1 mole of the acid anhydride used in the cyclization. Water can be used in large excess.

The resulting 3,4-dihydro-1,2,3-oxathiazin-4-one-2,2-dioxide compound represented by Formula (2) can be separated and purified by separation means such as distillation, concentration, extraction, crystallization, recrystallization and/or column chromatography. For example, the reaction mixture after the completion of the hydrolysis is separated into an organic layer and an aqueous layer, the target compound is recovered from the organic layer, and a solvent incompatible or immiscible with water is added to the aqueous layer to thereby extract and recover the target compound remained in the aqueous layer. Examples of the incompatible or immiscible solvent are the solvents to be used in the cyclization or esters of an organic mono- or dicarboxylic acid, such as the esters listed in the description of the reaction solvent. The organic layers including the extract from the aqueous layer are dried over a conventional desiccating agent such as sodium sulfate and are concentrated to thereby isolate the target compound. If necessary, the compound after concentration can be further purified typically by recrystallization.

The salt of the 3,4-dihydro-1,2,3-oxathiazin-4-one-2,2-dioxide compound represented by Formula (2) can be obtained by subjecting the compound represented by Formula (2), wherein $R^3$ is hydrogen atom, to a conventional salt forming reaction, such as a reaction with a base. Examples of the salt of the 3,4-dihydro-1,2,3-oxathiazin-4-one-2,2-dioxide compound represented by Formula (2) are metal salts, ammonium salts, and salts of organic bases. The types and preferred examples of the metal salts and organic bases are as in the salt of the beta-ketoamide-N-sulfonic acid represented by Formula (1). Typically preferred salts are salts of alkali metals such as sodium and potassium.

Such an alkali metal salt of the 3,4-dihydro-1,2,3-oxathiazin-4-one-2,2-dioxide compound represented by Formula (2) can be obtained by allowing the compound represented by Formula (2), wherein $R^3$ is hydrogen atom, to react with a base containing an alkali metal. Examples of the base herein are hydroxides of alkali metals, such as sodium hydroxide and potassium hydroxide; carbonates of alkali metals, such as sodium carbonate and potassium carbonate; and hydrogen carbonates of alkali metals, such as sodium hydrogen carbonate and potassium hydrogen carbonate.

The salt of the 3,4-dihydro-1,2,3-oxathiazin-4-one-2,2-dioxide compound represented by Formula (2) can be separated and purified by separation means such as concentration, extraction, crystallization, recrystallization and/or column chromatography.

Typical examples of the 3,4-dihydro-1,2,3-oxathiazin-4-one-2,2-dioxide compound represented by Formula (2) or a salt thereof are 6-($C_1$-$C_4$ alkyl)-3,4-dihydro-1,2,3-oxathiazin-4-one-2,2-dioxides such as 6-methyl-3,4-dihydro-1,2,3-oxathiazin-4-one-2,2-dioxide, 6-ethyl-3,4-dihydro-1,2,3-oxathiazin-4-one-2,2-dioxide, 6-n-propyl-3,4-dihydro-1,2,3-oxathiazin-4-one-2,2-dioxide and 6-i-propyl-3,4-dihydro-1,2,3-oxathiazin-4-one-2,2-dioxide; 6-aryl-3,4-dihydro-1,2,3-oxathiazin-4-one-2,2-dioxides such as 6-phenyl-3,4-dihydro-1,2,3-oxathiazin-4-one-2,2-dioxide; 5,6-di-($C_1$-$C_4$ alkyl)-3,4-dihydro-1,2,3-oxathiazin-4-one-2,2-dioxides such as 5-methyl-6-methyl-3,4-dihydro-1,2,3-oxathiazin-4-one-2,2-dioxide and 5-methyl-6-ethyl-3,4-dihydro-1,2,3-oxathiazin-4-one-2,2-dioxide; 5-aryl-6-($C_1$-$C_4$ alkyl)-3,4-dihydro-1,2,3-oxathiazin-4-one-2,2-dioxides such as 5-phenyl-6-methyl-3,4-dihydro-1,2,3-oxathiazin-4-one-2,2-dioxide; 5-($C_1$-$C_4$ alkyl)-6-aryl-3,4-dihydro-1,2,3-oxathiazin-4-one-2,2-dioxides such as 5-methyl-6-phenyl-3,4-dihydro-1,2,3-oxathiazin-4-one-2,2-dioxide; 6-($C_3$-$C_8$ cycloalkyl)-3,4-dihydro-1,2,3-oxathiazin-4-one-2,2-dioxides such as 6-cyclopentyl-3,4-dihydro-1,2,3-oxathiazin-4-one-2,2-dioxide and 6-cyclohexyl-3,4-dihydro-1,2,3-oxathiazin-4-one-2,2-dioxide; 5-($C_3$-$C_8$ cycloalkyl)-6-($C_1$-$C_4$ alkyl)-3,4-dihydro-1,2,3-oxathiazin-4-one-2,2-dioxides such as 5-cyclopentyl-6-methyl-3,4-dihydro-1,2,3-oxathiazin-4-one-2,2-dioxide and 5-cyclohexyl-6-methyl-3,4-dihydro-1,2,3-oxathiazin-4-one-2,2-dioxide; 5-($C_1$-$C_4$ alkyl)-6-($C_3$-$C_8$ cycloalkyl)-3,4-dihydro-1,2,3-oxathiazin-4-one-2,2-dioxides such as 5-methyl-6-cyclopentyl-3,4-dihydro-1,2,3-oxathiazin-4-one-2,2-dioxide and 5-methyl-6-cyclohexyl-3,4-dihydro-1,2,3-oxathiazin-4-one-2,2-dioxide; 6-($C_2$-$C_4$ alkenyl)-3,4-dihydro-1,2,3-oxathiazin-4-one-2,2-dioxides such as 6-vinyl-3,4-dihydro-1,2,3-oxathiazin-4-one-2,2-dioxide; 6-($C_2$-$C_6$ acyl)-3,4-dihydro-1,2,3-oxathiazin-4-one-2,2-dioxides such as 6-acetyl-3,4-dihydro-1,2,3-oxathiazin-4-one-2,2-dioxide, and salts of these compounds.

Among them, 3,4-dihydro-1,2,3-oxathiazin-4-one-2,2-dioxide compounds of Formula (2) wherein $R^1$ is methyl group, such as 6-methyl-3,4-dihydro-1,2,3-oxathiazin-4-one-2,2-dioxide, are preferred, since some of their physiologically acceptable salts, such as salts with Na, K or Ca, are used as sweeteners in the food industry, of which a potassium salt is typically useful as Acesulfame (Acesulfame potassium).

Figure 2:
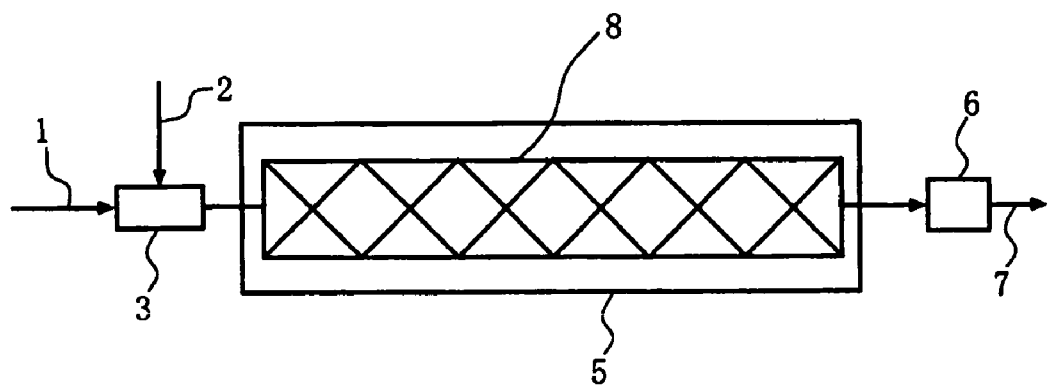
FIG. 2 is a schematic diagram of another example of the production equipment for use in the production method according to the present invention.

FIGS. 1 and 2 show non-restrictive examples of apparatuses for use in the present invention. FIG. 1 shows an embodiment of the production apparatus in which a tubular reactor is used in the cyclization. In this embodiment, a mixture containing the substrate and a mixture containing the acid anhydride are continuously fed from a conduit 1 and a conduit 2, respectively, via a premixer 3 to a tubular reactor 4 for reaction. The premixer 3 can be a simple piping joint or a mixer having a miniature stirrer, an ultrasonic mixer, or a motionless mixer such as a static mixer. The premixer 3 can be omitted. The tubular reactor 4 has a refrigerant jacket or refrigerant tank 5 for cooling (heat removal). The reaction mixture after cyclization is continuously taken out of the tubular reactor 4, is introduced to a hydrolysis reactor 6, is subjected to hydrolysis therein, and the reaction mixture after hydrolysis is discharged out of a chute piping 7. The hydrolysis can be carried out according to any system such as continuous system, batch system or semi-batch system. The feed piping of water for use in, for example, the continuous system is omitted in the figure. The hydrolysis reactor 6 can be a general stirring tank, as well as a continuous reactor for use in the cyclization.

FIG. 2 shows an embodiment of the production apparatus when the cyclization is carried out with the use of a motionless mixer such as a static mixer. In this embodiment, a mixture containing the substrate and a mixture containing the acid anhydride are continuously fed from a conduit 1 and a conduit 2, respectively, via a premixer 3 to a motionless mixer 8 for reaction. The premixer 3 can be any of those mentioned above. The premixer 3 can be omitted. The motionless mixer 8 has a refrigerant jacket or refrigerant tank 5 for cooling (heat removal). The reaction mixture after cyclization is continuously taken out of the motionless mixer 8, is introduced to a hydrolysis reactor 6, is subjected to hydrolysis therein, and the reaction mixture after hydrolysis is discharged out of a chute piping 7. The hydrolysis can be carried out according to any system such as continuous system or batch system. The aforementioned hydrolysis reactor 6 can be used herein.

The present invention will be illustrated in further detail with reference to several examples below, which are not intended to limit the scope of the invention.

EXAMPLE 1

A reaction was carried out using, as the reactor, a stainless steel tube having an inner diameter of 2 mm and an effective length of 1 m. A total of 55 mmol of triethylammonium acetoacetamide-N-sulfonate was dissolved in 112 g of dichloromethane and was cooled to 4° C. Separately, 324 mmol of sulfuric anhydride was dissolved in 278 g of dichloromethane and was cooled to 4° C. The triethylammonium acetoacetamide-N-sulfonate solution and the sulfuric anhydride solution were continuously fed at rates of 4.2 ml/min and 6.4 ml/min, respectively, into the reactor immersed in a refrigerant at −30° C. The residence time was 18 seconds. The reaction mixture was continuously sampled from the reactor, was introduced into 120 g of water which had been cooled to 0° C. in an Erlenmeyer flask and was subjected to hydrolysis at temperatures of 0° C. to 10° C. with stirring using a magnetic stirrer. After the completion of the reaction, the reaction mixture was separated into a dichloromethane layer and an aqueous layer, and the aqueous layer was further extracted with two portions of 100 ml of dichloromethane. The amount of 6-methyl-3,4-dihydro-1,2,3-oxathiazin-4-one-2,2-dioxide in the combined dichloromethane layers was determined by HPLC to find that the yield was 75% on the basis of triethylammonium acetoacetamide-N-sulfonate.

EXAMPLE 2

A reaction was carried out using, as the reactor, a stainless steel tube having an inner diameter of 2 mm and an effective length of 1 m and equipped with a Kenics static mixer as a mixer for raw materials (premixer). The Kenics static mixer had an inner diameter of 3.4 mm and a length of 10 cm and contained 17 elements. A total of 55 mmol of triethylammonium acetoacetamide-N-sulfonate was dissolved in 314 g of dichloromethane and was cooled to 4° C. Separately, 317 mmol of sulfuric anhydride was dissolved in 575 g of dichloromethane and was cooled to 4° C. The triethylammonium acetoacetamide-N-sulfonate solution and the sulfuric anhydride solution were continuously fed at rates of 5.1 ml/min and 7.0 ml/min, respectively, into the premixer arranged at an inlet of the reactor immersed in a refrigerant at −30° C. The residence times in the premixer and in the reactor were 4.5 seconds and 16 seconds, respectively. The reaction mixture was continuously sampled from the reactor, was introduced into 120 g of water which had been cooled to 0° C. in an Erlenmeyer flask and was subjected to hydrolysis at temperatures of 0° C. to 10° C. with stirring using a magnetic stirrer. After the completion of the reaction, the reaction mixture was separated into a dichloromethane layer and an aqueous layer, and the aqueous layer was further extracted with two portions of 300 ml of dichloromethane. The amount of 6-methyl-3,4-dihydro-1,2,3-oxathiazin-4-one-2,2-dioxide in the combined dichloromethane layers was determined by HPLC to find that the yield was 89% on the basis of triethylammonium acetoacetamide-N-sulfonate.

EXAMPLE 3

A reaction was carried out using, as the reactor, a Kenics static mixer having an inner diameter of 3.4 mm and a length of 10 cm and containing 17 elements. A total of 28 mmol of triethylammonium acetoacetamide-N-sulfonate was dissolved in 273 g of dichloromethane and was cooled to 4° C. Separately, 157 mmol of sulfuric anhydride was dissolved in 439 g of dichloromethane and was cooled to 4° C. The triethylammonium acetoacetamide-N-sulfonate solution and the sulfuric anhydride solution were continuously fed at rates of 5.1 ml/min and 7.4 ml/min, respectively, into the reactor immersed in a refrigerant at −30° C. The residence time was 4.3 seconds. The reaction mixture was continuously sampled from the reactor, was introduced into 120 g of water which had been cooled to 0° C. in an Erlenmeyer flask and was subjected to hydrolysis at temperatures of 0° C. to 10° C. with stirring using a magnetic stirrer. After the completion of the reaction, the reaction mixture was separated into a dichloromethane layer and an aqueous layer, and the aqueous layer was further extracted with two portions of 300 ml of dichloromethane. The amount of 6-methyl-3,4-dihydro-1,2,3-oxathiazin-4-one-2,2-dioxide in the combined dichloromethane layers was determined by HPLC to find that the yield was 84% on the basis of triethylammonium acetoacetamide-N-sulfonate.

EXAMPLE 4

A reaction was carried out using, as the reactor, a Kenics static mixer having an inner diameter of 3.4 mm and a length of 10 cm and containing 17 elements. A total of 28 mmol of triethylammonium acetoacetamide-N-sulfonate was dissolved in 362 g of dichloromethane and was cooled to 4° C. Separately, 139 mmol of sulfuric anhydride was dissolved in 585 g of dichloromethane and was cooled to 4° C. The triethylammonium acetoacetamide-N-sulfonate solution and the sulfuric anhydride solution were continuously fed at rates of 5.5 ml/min and 7.4 ml/min, respectively, into the reactor immersed in a refrigerant at −30° C. The residence time was 4.2 seconds. The reaction mixture was continuously sampled from the reactor, was introduced into 120 g of water which had been cooled to 0° C. in an Erlenmeyer flask and was subjected to hydrolysis at temperatures of 0° C. to 10° C. with stirring using a magnetic stirrer. After the completion of the reaction, the reaction mixture was separated into a dichloromethane layer and an aqueous layer, and the aqueous layer was further extracted with two portions of 300 ml of dichloromethane. The amount of 6-methyl-3,4-dihydro-1,2,3-oxathiazin-4-one-2,2-dioxide in the combined dichloromethane layers was determined by HPLC to find that the yield was 86% on the basis of triethylammonium acetoacetamide-N-sulfonate.

EXAMPLE 5

A reaction was carried out using, as the reactor, a Kenics static mixer having an inner diameter of 8.0 mm and a length of 26 cm and containing 17 elements. A total of 19 mmol of triethylammonium acetoacetamide-N-sulfonate was dissolved in 250 g of dichloromethane and was cooled to 3° C. Separately, 109 mmol of sulfuric anhydride was dissolved in 404 g of dichloromethane and was cooled to 3° C. The triethylammonium acetoacetamide-N-sulfonate solution and the sulfuric anhydride solution were continuously fed at rates of 71 ml/min and 103 ml/min, respectively, into the reactor immersed in a refrigerant at −30° C. The residence time was 4.5 seconds. The reaction mixture was continuously sampled from the reactor, was introduced into 120 g of water which had been cooled to 0° C. in an Erlenmeyer flask and was subjected to hydrolysis at temperatures of 0° C. to 10° C. with stirring using a magnetic stirrer. After the completion of the reaction, the reaction mixture was separated into a dichloromethane layer and an aqueous layer, and the aqueous layer was further extracted with two portions of 300 ml of dichloromethane. The amount of 6-methyl-3,4-dihydro-1,2,3-oxathiazin-4-one-2,2-dioxide in the combined dichloromethane layers was determined by HPLC to find that the yield was 85% on the basis of triethylammonium acetoacetamide-N-sulfonate.

EXAMPLE 6

A reaction was carried out using, as the reactor, a stainless steel tube having an inner diameter of 0.5 mm and an effective length of 2 m. A total of 28 mmol of triethylammonium acetoacetamide-N-sulfonate was dissolved in 363 g of dichloromethane and was cooled to 4° C. Separately, 157 mmol of sulfuric anhydride was dissolved in 583 g of dichloromethane and was cooled to 4° C. The triethylammonium acetoacetamide-N-sulfonate solution and the sulfuric anhydride solution were continuously fed at rates of 2.1 ml/min and 3.2 ml/min, respectively, into the reactor immersed in a refrigerant at −30° C. The residence time was 4.4 seconds. The reaction mixture was continuously sampled from the reactor, was introduced into 120 g of water which had been cooled to 0° C. in an Erlenmeyer flask and was subjected to hydrolysis at temperatures of 0° C. to 10° C. with stirring using a magnetic stirrer. After the completion of the reaction, the reaction mixture was separated into a dichloromethane layer and an aqueous layer, and the aqueous layer was further extracted with two portions of 300 ml of dichloromethane. The amount of 6-methyl-3,4-dihydro-1,2,3-oxathiazin-4-one-2,2-dioxide in the combined dichloromethane layers was determined by HPLC to find that the yield was 87% on the basis of triethylammonium acetoacetamide-N-sulfonate.

EXAMPLE 7

A reaction was carried out using, as the reactor, a stainless steel tube having an inner diameter of 4 mm and an effective length of 2 m. The reactor was equipped with a Kenics static mixer having an inner diameter of 8.0 mm and a length of 26 cm and containing 17 elements as a mixer for raw materials (premixer), had an insert tube at piping joint of a raw material mixing section, in which two liquids start to be mixed in the static mixer section. A total of 60 mmol of triethylammonium acetoacetamide-N-sulfonate was dissolved in 300 g of dichloromethane and was cooled to −10° C. Separately, 382 mmol of sulfuric anhydride was dissolved in 418 g of dichloromethane and was cooled to −10° C. The triethylammonium acetoacetamide-N-sulfonate solution and the sulfuric anhydride solution were continuously fed at rates of 141 ml/min and 199 ml/min, respectively, into the premixer arranged at an inlet of the reactor immersed in a refrigerant at −30° C. The residence times in the premixer and in the reactor were 2.3 seconds and 4.4 seconds, respectively. The reaction mixture was continuously sampled from the reactor, was introduced into 60 g of water in an Erlenmeyer flask and was subjected to hydrolysis at temperatures of 15° C. to 25° C. with stirring using a magnetic stirrer. After the completion of the reaction, the reaction mixture was separated into a dichloromethane layer and an aqueous layer, and the aqueous layer was further extracted with two portions of 200 ml of dichloromethane. The amount of 6-methyl-3,4-dihydro-1,2,3-oxathiazin-4-one-2,2-dioxide in the combined dichloromethane layers was determined by HPLC to find that the yield was 91% on the basis of triethylammonium acetoacetamide-N-sulfonate.

EXAMPLE 8

A reaction was carried out using, as the reactor, a stainless steel tube having an inner diameter of 4 mm and an effective length of 2 m. This reactor was equipped with a Kenics static mixer having an inner diameter of 8.0 mm and a length of 26 cm and containing 17 elements as a mixer for raw materials (premixer) and had an insert tube at piping joint of a raw material mixing section, in which two liquids start to be mixed in the static mixer section. A total of 134 mmol of triethylammonium acetoacetamide-N-sulfonate was dissolved in 400 g of dichloromethane and was cooled to −10° C. Separately, 950 mmol of sulfuric anhydride was dissolved in 533 g of dichloromethane and was cooled to −10° C. The triethylammonium acetoacetamide-N-sulfonate solution and the sulfuric anhydride solution were continuously fed at rates of 139 ml/min and 193 ml/min, respectively, into the premixer arranged at an inlet of the reactor immersed in a refrigerant at −30° C. The residence times in the premixer and in the reactor were 2.4 seconds and 4.5 seconds, respectively. The reaction mixture was continuously sampled from the reactor, was introduced into 60 g of water in an Erlenmeyer flask and was subjected to hydrolysis at temperatures of 15° C. to 35° C. with stirring using a magnetic stirrer. After the completion of the reaction, the reaction mixture was separated into a dichloromethane layer and an aqueous layer, and the aqueous layer was further extracted with two portions of 200 ml of dichloromethane. The amount of 6-methyl-3,4-dihydro-1,2,3-oxathiazin-4-one-2,2-dioxide in the combined dichloromethane layers was determined by HPLC to find that the yield was 85% on the basis of triethylammonium acetoacetamide-N-sulfonate.

COMPARATIVE EXAMPLE 1

A glass WFE having an inner diameter of 5 cm and a length of 20 cm and equipped with three wipers was used as the reactor. A total of 40 mmol of triethylammonium acetoacetamide-N-sulfonate was dissolved in 60 g of dichloromethane and was cooled to 0° C. Separately, 229 mmol of sulfuric anhydride was dissolved in 94 g of dichloromethane and was cooled to 0° C. A refrigerant at −30° C. was allowed to flow into the jacket of the reactor, and the wipers were rotated at a rate of 700 rpm. The triethylammonium acetoacetamide-N-sulfonate solution and the sulfuric anhydride solution were continuously added dropwise to the stirring axis of the wipers and to the wall of the WFE reactor, respectively, over sixteen minutes for reaction. The reaction mixture discharged from the bottom of the WFE reactor was continuously fed to 20 g of water in a flask cooled to 0° C. on an ice bath, and the mixture was subjected to hydrolysis at 0° C. to 10° C. with stirring using a magnetic stirrer. After the completion of the reaction, 100 g of dichloromethane and 10 g of water were added, the mixture was stirred and was separated into a dichloromethane layer and an aqueous layer. The aqueous layer was further extracted with two portions of 100 ml of dichloromethane. The amount of 6-methyl-3,4-dihydro-1,2,3-oxathiazin-4-one-2,2-dioxide in the combined dichloromethane layers was determined by HPLC to find that the yield was 37% on the basis of triethylammonium acetoacetamide-N-sulfonate.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method for producing a 3,4-dihydro-1,2,3-oxathiazin-4-one-2,2-dioxide compound represented by the following formula (2):

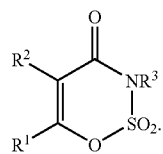

(2)

wherein $R^1$ and $R^2$ are the same as or different from each other and are each a hydrogen atom, alkyl group, alkenyl group, alkynyl group, cycloalicyl group, acyl group, aralkyl group or aryl group; and $R^3$ is a hydrogen atom, alkyl group, alkenyl group, alkynyl group, cycloalkyl group, acyl group, aralkyl group or aryl group, or a salt thereof, the method comprising the step of subjecting a beta-ketoainide-N-sulfonic acid represented by the following Formula (1):

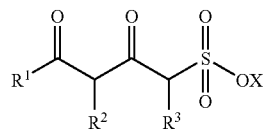

(1)

wherein $R^1$, $R^2$ and $R^3$ are as defined above; and X is a hydrogen atom, or a salt thereof, to cyclization in the presence of an acid anhydride with or without further subjecting the cyclized product to hydrolysis, wherein the cyclization is continuously carried out using a continuous flow reactor selected from a tubular reactor or a motionless mixer having a tube in the tubular reactor or the motionless mixer having an inner diameter of from 0.2 to 30 millimeters, wherein the beta-ketoamide-N-sulfonic acid or the salt thereof and the acid anhydride are cooled to −100° C. to 10° C. before the cyclization, an amount of the acid anhydride for use in the cyclization is 1 to 20 moles per 1 mole of the beta-ketoamide-N-sulfonic acid or the salt thereof, and wherein a premixer selected from the group consisting of a stirred mixer, an ultrasonic mixer, a static mixer and a piping joint is optionally employed with the continuous flow reactor, and when a premixer is employed, a residence time in the premixer ranges from 0.1 to 10 second, and the residence time in the continuous flow reactor ranges from 0.001 to 60 seconds, and when the continuous flow reactor is used without a premixer, the residence time in the continuous flow reactor ranges from 0.1 to 10 seconds.

2. The method according to claim 1, further comprising using, as the reactor, a tubular reactor or a motionless mixer having at least one stirred mixer, an ultrasonic mixer or motionless mixer in an inlet part of the reactor.

3. The method according to claim 1, further comprising using an acid anhydride derived from at least one acid selected from the group consisting of sulfuric acid, sulfonic acids, halogenated sulfuric acids, pyrophosphoric acids, nitric acid and boric acids as the acid anhydride.

4. The method according to claim 2 or 3, wherein the 3,4-dihydro-1,2,3-oxathiazin-4-one-2,2-dioxide compound is 6-methyl-3,4-dihydro-1,2,3-oxathiazin -4-one-2,2-dioxide.

* * * * *